United States Patent [19]

Fritschi et al.

[11] Patent Number: 4,461,895
[45] Date of Patent: Jul. 24, 1984

[54] DIBENZO(DE,G)QUINOLINES

[75] Inventors: Edgar Fritschi, St. Peter; Johannes Hartenstein, Stegen-Wittental; Wolfgang Heidt, Emmendingen; Gerhard Satzinger, Denzlingen, all of Fed. Rep. of Germany

[73] Assignee: Warner-Lambert Company, Morris Plains, N.J.

[21] Appl. No.: 375,937

[22] Filed: May 7, 1982

[30] Foreign Application Priority Data

May 9, 1981 [DE] Fed. Rep. of Germany ....... 3118521

[51] Int. Cl.$^3$ .......................................... C07D 221/18
[52] U.S. Cl. ...................................... 546/75; 424/257
[58] Field of Search .......................... 546/75; 424/258

[56] References Cited

U.S. PATENT DOCUMENTS 3,717,643  2/1973  Archer .................................. 546/75
4,309,542  1/1982  Hartenstein et al. ................. 546/75

OTHER PUBLICATIONS

Neumeyer et al., J. Med. Chem., 1981, 24, pp. 1440–1445.

Primary Examiner—Paul M. Coughlan, Jr.
Attorney, Agent, or Firm—Ronald A. Daignault

[57] ABSTRACT

The present invention provides dibenzo(de,g)quinoline derivatives of the general formula:

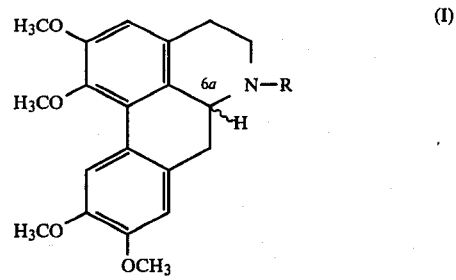

wherein R is an unsaturated aliphatic hydrocarbon radical containing up to 6 carbon atoms or a cycloalkylalkyl radical containing 4 to 6 carbon atoms; and the pharmacologically acceptable salts thereof.

The present invention also provides processes for the preparation of these compounds and pharmaceutical compositions containing them. Furthermore, the present invention is concerned with the use of these compounds for combating colds and allergies.

3 Claims, No Drawings

DIBENZO(DE,G)QUINOLINES

The present invention is concerned with new dibenzo(de,g)quinoline derivatives, with the preparation thereof and with pharmaceutical compositions containing them.

The new dibenzo(de,g)quinoline derivatives according to the present invention are compounds of the general formula:

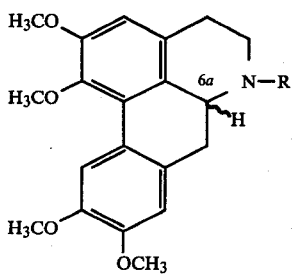

wherein R is an unsaturated aliphatic hydrocarbon radical containing up to 6 carbon atoms or a cycloalkylalkyl radical containing 4 to 6 carbon atoms; and the pharmacologically-acceptable salts thereof.

The wavy line in the 6a-position of the compounds of general formula (I) means that the compounds can be either in racemic form or can also occur as enantiomers, those compounds with a 6aS-configuration being preferred.

Those compounds of general formula (I) are preferred in which R is an unsaturated aliphatic hydrocarbon radical containing 3 to 6 carbon atoms or a cycloalkylalkyl radical containing 4 to 6 carbon atoms.

More, particularly, R is preferably, for example, an allyl, methallyl, dimethylallyl, but-2-enyl, 3-methbut-3-enyl, propargyl, cyclopropylmethyl, cyclobutylmethyl or cyclopentylmethyl radical.

The compounds (I) according to the present invention can be prepared, for example, by one of the following methods:

(a) a compound of the general formula:

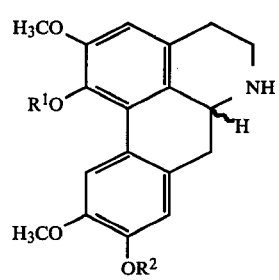

in which R¹ and R², which may be the same or different, are hydrogen atoms or methyl radicals, is N-alkenylated, N-alkynylated or N-cycloalkylalkylated, whereafter, when R¹ and/or R² is a hydrogen atom, the product obtained is O-methylated; or (b) a compound of the general formula:

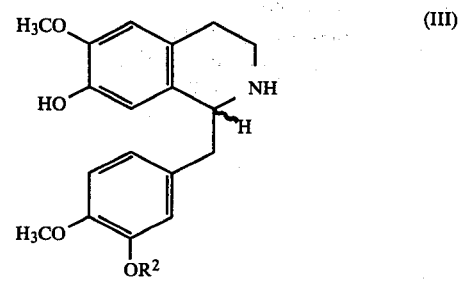

in which R² is a hydrogen atom or a methyl radical, is N-alkenylated, N-alkynylated or N-cycloalkylalkylated, then cyclised and subsequently O-methylated.

The N-alkenylation, N-alkynylation or N-cycloalkylalkylation of compounds (II) and (III) can take place by methods known for the N-alkenylation, N-alkynylation and N-cycloalkylalkylation of secondary amines, the most simple method being by means of reactive derivatives of the general formula:

$$X-R \qquad (IV),$$

in which R has the same meaning as above and X is a halogen atom.

Furthermore, it is also possible to introduce the substituent R as an acyl radical with the appropriate number of carbon atoms, the amide so obtained then being converted into the substituent R by reduction of the carbonyl group. The use of complex hydrides, for example of lithium aluminium hydride or of sodium dihydrido-bis-(2-methoxyethoxy)-aluminate, has proved to be useful for this reduction. Apart from the amide carbonyl group, any phenol ester groups possibly present, which have been formed in the case of the acylation of phenolic amines, are thereby also reduced, with the reformation of the free phenols.

The cyclisation of the tetrahydroisoquinolines of general formula (III) and of the N-alkenyl, N-alkynyl, N-cycloalkylalkyl and N-acyl derivatives thereof takes place by means of the usual processes of oxidative phenol coupling. According to the present invention, the oxidative cyclisation of 7-hydroxytetrahydroisoquinolines with vanadium oxytrichloride according to the method described in Federal Republic of Germany Patent Specification No. 27 57 281 is especially advantageous.

The O-methylation of the N-alkenyl-, N-alkynyl-, N-cycloalkylalkyl- and N-acylnoraporphines can be carried out by processes conventionally used for the O-alkylation of phenols, for example by methylation with diazomethane or dimethyl sulphate. However, O-methylation with basic phenyltrimethylammonium compounds according to the method described in Federal Republic of Germany Patent Specification No. 27 57 335 has proved to be especially advantageous.

The compounds of general formula (II) serving as starting materials for the preparation of compounds of general formula (I) according to the present invention are known compounds. They can be obtained, for example, by the oxidative cyclisation (see Federal Republic of Germany Patent Specification No. 27 57 281) and O-methylation of 1-hydroxy-N-noraporphine or of its N-trifluoroacetyl derivative (for example according to the method described in Federal Republic of Germany Patent Specification No. 27 57 335; or according to J. Org. Chem., 41, 4049/1976).

The tetrahydroisoquinolines of general formula (III) used as starting materials in process (b) are also known compounds, i.e. N-norreticuline (R=H) and N-norcodamine (R=CH$_3$). The synthesis of racemic and optically-active N-norreticuline is described by K. C. Rice and A. Brossi (J. Org. Chem., 45, 592/1980) and the preparation of racemic norcodamine is disclosed in J. Org. Chem., 41, 4049/1976 (footnote 6).

The working up of the reaction products, as well as the isolation and purification of the compounds (I), is carried out in known manner, for example, by crystallisation in the form of the bases or of acid-addition compounds, optionally after previous chromatographic purification.

Another advantageous route for the preparation of the enantiomers is, in the case of processes (a) and (b), starting from optically-active compounds of general formula (II) or (III). An especially preferred starting material is the compound of general formula (III), wherein R$^2$ is a methyl radical, since it can be separated into the optical antipodes with (+)-and (−)-anilinotartaric acids (see J. Org. Chem., 33, 3993/1968) and especially with o-bromoanilinotartaric acid, or with N-acetyl-L-leucine. In comparison with N-norreticuline (III; R$^2$=H), the optical separation of which with bromoanilinotartaric acid has been described in the literature (see J. Org. Chem., 45, 592/1980), this starting material has the advantage of being easily prepared from inexpensive materials. Furthermore, in the case of the oxidative cyclisation to aporphine with vanadium oxytrichloride according to process (b), less by-products are formed.

The compounds of general formula (I) can be in racemic or optically-active form. The optically-active forms can be prepared in known manner, for example by fractional crystallisation of the diastereomeric salts.

The conversion of the free bases of general formula (I) into their pharmacologically-acceptable salts takes place by neutralisation with appropriate organic or inorganic acids, for example hydrochloric acid, sulphuric acid, phosphoric acid, hydrobromic acid, acetic acid, fumaric acid, oxalic acid, lactic acid, citric acid, malic acid, salicylic acid, malonic acid, maleic acid, succinic acid, tartaric acid or ascorbic acid.

For the preparation of pharmaceutical compositions, the active materials are worked up with conventional additives and liquid or solid carrier materials. The compounds (I) can be administered orally and parenterally in liquid or solid form within wide dosage ranges.

Conventional additives for liquid forms include, for example, tartrate and citrate buffers, ethanol, complex formers (for example ethylenediamine-tetraacetic acid and the non-toxic salts thereof) and high molecular weight polymers (such as liquid polyethylene oxide) for viscosity regulation. Solid carrier materials include, for example, starch, lactose, mannitol, methyl cellulose, talc, highly dispersed silicic acids, high molecular weight fatty acids (for example stearic acid), gelatine, agar-agar, calcium phosphate, magnesium stearate, animal and vegetable fats and solid high molecular weight polymers (for example polyethylene glycol). Compositions suitable for oral administration can, if desired, contain flavouring and/or sweetening materials.

The compounds of general formula (I) possess valuable pharmacological properties. In particular, they exhibit antitussive, analgesic, anti-allergic and neuroleptic actions and inhibit the aggregation of blood platelets. The new compounds thereby considerably exceed the known antitussive action of 5,6,6a,7-tetrahydro-1,2,9,10-tetramethoxy-5-methyl-4H-dibenzo(de,g)quinoline (glaucine) with regard to the strength and length of activity. Thus, in the coughing experiment according to Domenjoz (Arch. f. Pathol. u. Pharmakol., 19, 215/1952) on cats, the compound of Example 1, in the case of the intravenous administration of 1 mg./kg. body weight, gives an inhibition of coughing lasting 20 minutes, whereas the standard compound glaucine, at a dosage of 2 mg./kg. i.v., only inhibits coughing for 10 minutes.

The following Table summarises some of the animal experimental results obtained:

| Compound | dosage and antitussive effect in experiments on cats | toxicity in mice LD$_{50}$ in mg./kg. |
|---|---|---|
| glaucine | 2.0 mg./kg., i.v.: 10 min. cough inhibition | 58.3 i.v. |
| | 10.0 mg./kg., sc.: no cough inhibition | 20.0 sc. |
| | 4.0 mg./kg., id.: 40 min. cough inhibition | 530.6 ig. |
| Example 1 | 1.0 mg./kg., i.v.: 20 min. cough inhibition | 150.0 i.v. |
| | 6.25 mg./kg., sc.: 40 min. cough inhibition | 150.0 sc. |
| | 6.25 mg./kg., id.: 90 min. cough inhibition | about 1200.0 ig. |

Depending upon the indications, the peroral individual dose of the compounds (I) is in the range of from 30 to 200 mg., which can be administered up to three times daily.

The following Examples are given for the purpose of illustrating the present invention:

EXAMPLE 1

(+)-6-Allyl-5,6,6a,7-tetrahydro-1,2,9,10-tetramethoxy-4H-dibenzo(de,g)quinoline

Variant 1.

3.6 g. (11.4 mmol) (−)-7-Hydroxy-1-(3-hydroxy-4-methoxybenzyl)-6-methoxy-1,2,3,4-tetrahydroisoquinoline (see J. Org. Chem., 45, 592/1980) in 70 ml. ethanol are mixed, while stirring, with 0.88 ml. (1.26 g., 10.4 mmol) allyl bromide and 2.3 g. (27.4 mmol) sodium bicarbonate. The reaction mixture is stirred for 30 minutes at ambient temperature and then heated to 80° C. for 3 hours. After cooling, it is evaporated in a vacuum and the residue is partitioned between water and methylene chloride. The usual working up and chromatography on silica gel with chloroform as elution agent gives 3.3 g. (+)-2-allyl-7-hydroxy-1-(3-hydroxy-4-methoxybenzyl)-1,2,3,4-tetrahydroisoquinoline as a TLC-uniform foam.

MS: m/e (M+) base peak m/e 218 $[\alpha]_D^{RT} = +83°$ (c=1, chloroform).

The total amount of the product obtained is dissolved, while cooling with ice water and with the exclusion of moisture, in a mixture of 30 ml. trifluoroacetic acid and 30 ml. anhydrous methylene chloride. A solution of 1.33 ml. (2.45 g., 14.12 mmol) vanadium oxytrichloride in 30 ml. anhydrous methylene chloride is added dropwise within the course of about 5 minutes to this solution, while stirring at −10° C. and under an inert gas atmosphere. The reaction mixture is further stirred for 10 minutes at −10° C. and for 30 minutes at 0° C. Thereafter, it is evaporated at ambient temperature in a rotary evaporator and the residue is partitioned between ice water and chloroform. The base is liberated from the chloroform phase with a dilute aqueous solution of ammonia. After working up and crystallising from chloroform/diethyl ether, there is obtained (+)-6-allyl-5,6,6a,7-tetrahydro-1,9-dihydroxy-2,10-dimethoxy-4H-dibenzo(de,g)quinoline; m.p. 161°–171° C.

MS: m/e 353 (M+) $[\alpha]_D^{RT} = +34.6°$ (c=0.5, methanol).

1.69 g. (4.78 mmol) (+)-6-Allyl-5,6,6a,7-tetrahydro-a,9-dihydroxy-2,10-dimethoxy-4H-dibenzo(de,g)quinoline are dissolved in a 100 ml. of a mixture of toluene and dimethylformamide (9:1 v/v) and heated to 100° C. 17 ml. of a 1N solution of phenyltrimethylammonium hydroxide in methanol are added dropwise thereto in the course of about 10 minutes with vigorous stirring and the simultaneous distilling off of the methanol/toluene azeotrope formed. After completion of the addition, the reaction mixture is heated until the temperature of the distillate passing over has reached about 111° C., whereafter heating under reflux is continued for 1 hour. If, according to the TLC analysis, starting material is still present, then a further portion of methylating solution is added thereto and then further processed as described above. For the isolation of the product, the reaction mixture is filtered and the filtrate is evaporated in a vacuum. After partitioning the residue between water and methylene chloride and the usual working up, the crude product obtained is chromatographed on silica gel with the use of chloroform as elution agent and then converted into the hydrochloride with ethanolic hydrogen chloride solution; m.p. 214°–220° C.

$C_{23}H_{27}NO_4 \cdot HCl \cdot \frac{1}{4} H_2O$ calc.: C 65.40%; H 6.80%; Cl 8.39%; N 3.32% found: 65.31%; 6.81%; 8.64%; 3.33% $[\alpha]_D^{22} = +118.6°$ (c=0.5; chloroform).

The (+)-6-allyl-5,6,6a,7-tetrahydro-1,9-dihydroxy-2,10-dimethoxy-4H-dibenzo(de,g)quinoline obtained as intermediate can also be prepared in the following manner:

582 mg. (1.85 mmol) (+)-5,6,6a,7-Tetrahydro-1,9-dihydroxy-2,10-dimethoxy-4H-dibenzo(de,g)quinoline are dissolved in 10 ml. dimethylformamide. After the addition of 385 mg. (4.58 mmol) sodium bicarbonate and 0.2 ml. (279.6 mg.; 2.31 mmol) allyl bromide, the reaction mixture is stirred for 30 minutes at ambient temperature and thereafter heated under reflux for 2 hours. Subsequently, the solvent is evaporated off in a vacuum and the residue is partitioned between chloroform and water. After working up and crystallising from chloroform/diethyl ether, there is obtained (+)-6-allyl-5,6,6a,7-tetrahydro-1,9-dihydroxy-2,10-dimethoxy-4H-dibenzo(de,g)quinoline; m.p. 161°–171° C.

Variant 2.

4.5 g. (12.2 mmol) (+)-6-Allyl-5,6,6a,7-tetrahydro-1-hydroxy-2,9,10-trimethoxy-4H-dibenzo(de,g)quinoline are reacted in 230 ml. of a mixture of toluene and dimethylformamide (9:1 v/v) with 20 ml. of a 1N solution of phenyltrimethylammonium hydroxide in methanol as described in Variant 1. After appropriate working up, there is obtained (+)-6-allyl-5,6,6a,7-tetrahydro-1,2,9,10-tetramethoxy-4H-dibenzo(de,g)quinoline, which is identical in every respect to the product obtained according to Variant 1. $[\alpha]_D^{RT}$ (hydrochloride): +117.7° (c=0.5, methanol).

The (+)-6-allyl-5,6,6a,7-tetrahydro-1-hydroxy-2,9,10-trimethoxy-4H-dibenzo(de,g)quinoline used as starting material is prepared as follows:

(a) Racemate separation of 7-hydroxy-6-methoxy-1-(3,4-dimethoxybenzyl)-1,2,3,4-tetrahydroisoquinoline via the bromoanilinotartrate.

77 g. (0.233 mol) (±)-7-Hydroxy-6-methoxy-1-(3,4-dimethoxybenzyl)-1,2,3,4-tetrahydroisoquinoline (N-norcodamine; preparation: J. Org. Chem., 41, 4049/1976) are dissolved at about 50° C. in 200 ml. methanol and mixed with a solution of 75.9 g. (0.235 mol) (+)-2'-bromoanilinotartaric acid hydrate (J. Org. Chem., 33, 3993/1968) in 200 ml. methanol. The mixture is left to stand for 2 days at ambient temperature and then the colourless to yellowish crystals are filtered off with suction; m.p. 166°–172° C.

$[\alpha]_D^{RT} = +38.7°$ (c=0.5, methanol)

The base liberated from the salt in the usual manner is crystallised from ethanol; m.p. 156°–159° C.

$[\alpha]_D^{RT} = -40.6°$ (c=0.5, methanol) MS: m/e 329 (M+), base peak m/e 178.

(b) Racemate separation via the N-acetyl-L-leucinate.

18.9 g. (57.4 mmol) (±)-7-Hydroxy-6-methoxy-1-(3,4-dimethoxybenzyl)-1,2,3,4-tetrahydroisoquinoline are dissolved at 60° C. in 70 ml. methanol and mixed with a solution of 9.94 g. (57.4 mmol) N-acetyl-L-leucine in 50 ml. methanol, also heated to 60° C. The solution obtained is concentrated by evaporating in a vacuum. After the addition of isopropanol/diethyl ether and recrystallisation from the same solvent mixture, there is obtained the N-acetyl-L-leucinate of (−)-7-hydroxy-6-methoxy-1-(3,4-dimethoxybenzyl)-1,2,3,4-tetrahydroisoquinoline; m.p. 179°–186° C.

$[\alpha]_D^{RT} = -21.5° \pm 1°$ (c=0.5, water).

Conversion into the base and crystallisation from ethanol gives the title compound; m.p. 156°–159° C.

$[\alpha]_D^{RT} = -37.3°$ (c=0.5, methanol).

27.7 g. (84 mmol) (−)-7-Hydroxy-6-methoxy-1-(3,4-dimethoxybenzyl)-1,2,3,4-tetrahydroisoquinoline in 430 ml. ethanol are mixed with 9.18 g. (75.9 mmol) allyl bromide and 17.6 g. (209 mmol) sodium bicarbonate. The reaction mixture is heated for 3 hours at 80° C., while stirring. After cooling and evaporating in a vacuum, the residue is partitioned between water and methylene chloride. The usual working up and chromatographic purification (silica gel; chloroform) gives 22.0 g. of a pale yellow foam. By crystallisation from isopropanol-diethyl ether, there is obtained (+)-2-allyl-7-hydroxy-6-methoxy-1-(3,4-dimethoxybenzyl)-1,2,3,4-tetrahydroisoquinoline in the form of colourless crystals; m.p. 108°–112° C.

$[\alpha]_D^{RT} = +65.7°$ (c=1, chloroform) MS: m/e 369 (M+), base peak m/e 218.

22 g. (59.54 mmol) (+)-2-Allyl-7-hydroxy-6-methoxy-1-(3,4-dimethoxybenzyl)-1,2,3,4-tetrahydroisoquinoline in a mixture of 190 ml. trifluoroacetic acid and 190 ml. anhydrous methylene chloride are mixed at −10° C., with the exclusion of moisture, with a solution of 6.0 ml. (11.04 g., 63.7 mmol) vanadium oxytrichloride in 190 ml. anhydrous methylene chloride. The reaction mixture is stirred for 30 minutes at −10° C., for 1 hour at 0° C. and for 2 hours at ambient temperature. Thereafter, the reaction mixture is concentrated to about one third of its volume by evaporation of the solvent in a vacuum at ambient temperature. The residue is mixed with ice water and extracted with chloroform. The chloroform phase is rendered basic with an aqueous solution of ammonia and worked up in the usual manner. By crystallisation from ethanol, there is obtained (+)-6-allyl-5,6,6a,7-tetrahydro-1-hydroxy- 2,9,10-trimethoxy-4H-dibenzo(de,g)quinoline; m.p. 85°–93° C./134°–138° C.

MS: m/e 367 (M+) NMR: δ(CDCl$_3$), 3.93 (3×OCH$_3$), 5.0–6.2 (m, 3H, —CH=CH$_2$), 6.56 (s, 8–H), 6.80 (s, 3–H), 8.06 (s, 11–H)

Hydrochloride: m.p. 192°–210° C. Hydrobromide monohydrate: m.p. 214°–224° C.

Variant 3.

1 g. (1.94 mmol) (+)-N-Norglaucine (—)-N-acetyl-L-leucinate ([α]$_D^{20}$ = +33.4° (c 0.5, methanol)) are taken up in 25 ml. methylene chloride and converted into the base with a 5% aqueous solution of sodium bicarbonate. The methylene chloride extract is dried and evaporated in a vacuum and the residue is dissolved in 20 ml. anhydrous ethanol. After the addition of 400 mg. (4.76 mmol) sodium bicarbonate and 0.19 ml. (226 mg., 2.20 mmol) allyl bromide, the reaction mixture is stirred for 30 minutes at ambient temperature and then heated under reflux for 2 hours. After cooling, it is evaporated in a vacuum and the residue is partitioned between water and methylene chloride. The usual working up and crystallisation from ethanol gives (+)-6-allyl-5,6,6a,7-tetrahydro-1,2,9,10-tetramethoxy-4H-dibenzo(de,g)quinoline; m.p. 139°–143° C.

MS: m/e 381 (M+), base peak m/e 41 (CH$_2$=CH—CH$_2$+) IR (KBr) inter alia 920/985 cm$^{-1}$ (—CH=CH$_2$) NMR: δ(CDCl$_3$) 3.63 (s,1-OCH$_3$), 3.90 (3×OCH$_3$), 5.0–6.0 (m, 3H, CH=CH$_2$), 6.59 (s, 8–H), 6.76 (s, 3–H), 8.06 (s, 11–H).

By treatment with ethanolic hydrochloric acid, there is obtained the hydrochloride in the form of reddish crystals; m.p. 214°–220° C.

EXAMPLE 2

(—)-6-Allyl-5,6,6a,7-tetrahydro-1,2,9,10-tetramethoxy-4H-dibenzo(de,g)quinoline 8.0 g. (25.37 mmol) (+)-7-Hydroxy-1-(3-hydroxy-4-methoxybenzyl)-6-methoxy-1,2,3,4-tetrahydroisoquinoline (J. Org. Chem., 45, 592/1980) in 150 ml. ethanol are mixed with 5.10 g. (60.7 mmol) sodium bicarbonate and 2.19 ml. (3.07 g.) allyl bromide in a manner analogous to that described in Example 1. The N-allylation product (8.0 g., 22.5 mmol, yellowish foam) obtained after appropriate working up is reacted at −10° C. in a mixture of 70 ml. trifluoroacetic acid and 70 ml. methylene chloride with 3.2 ml. (5.89 g., 33.98 mmol) vanadium oxytrichloride in 35 ml. anhydrous methylene chloride in a manner analogous to that described in Example 1. The crude product obtained (8 g., crystallisation from chloroform/diethyl ether; m.p. 159°–165° C.) is O-methylated in a manner analogous to that described in Example 1 with 115 ml. of a 1N solution of phenyltrimethylammonium hydroxide in methanol in 400 ml. of a mixture of toluene and dimethylformamide (9:1 v/v). The crude product obtained after appropriate working up is, after chromatographic purification on silica gel with chloroform as elution agent, converted with ethanolic hydrochloric acid into the crystalline hydrochloride. There is obtained (—)-6-allyl-5,6,6a,7-tetrahydro-1,2,9,10-tetramethoxy-4H-dibenzo(de,g)quinoline hydrochloride; m.p. 210°–217° C.

[α]$_D^{RT}$ = −122° (c=0.5, chloroform) C$_{23}$H$_{27}$NO$_4$, HCl, ¼ H$_2$O calc.: C 65.40%; H 6.80%; Cl 8.39%; N 3.32% found: 65.26%; 6.53%; 8.64%; 3.35%.

EXAMPLE 3

(+)-5,6,6a,7-Tetrahydro-1,2,9,10-tetramethoxy-6-(3-methylbut-2-enyl)-4H-dibenzo(de,g)quinoline Methylation of (+)-5,6,6a,7-tetrahydro-1,9-dihydroxy-2,10-dimethoxy-6-(3-methylbut-2-enyl)-4H-dibenzo(de,g)quinoline with phenyltrimethylammonium hydroxide and working up in a manner analogous to that described in Example 1 gives (+)-5,6,6a,7-tetrahydro-1,2,9,10-tetramethoxy-6-(3-metylbut-2-enyl)-4H-dibenzo(de,g)quinoline in the form of the hydrochloride;

m.p. 214°–226° C. MS: m/e 409 (M+) NMR: δ(CDCl$_3$) 1.80 (b, 6H), 3.66 (1×OCH$_3$), 3.90 (3×OCH$_3$), 5.53 (m, 1H), 6.64 (s, 8–H), 6.80 (s, 3–H), 8.05 (s, 11–H).

By conversion into the base and reaction with L-(+)-tartaric acid, there is obtained the crystalline L-(+)-hydrogen tartrate; m.p. 115°–125° C./165°–176° C. C$_{25}$H$_{31}$NO$_4$·C$_4$H$_6$O$_6$ calc.: C 61.25%; H 6.73%; N 2.46% found: 62.23%; 6.62%; 2.42% [α]$_D^{RT}$ = +81.1° (c=0.5, chloroform).

The (+)-5,6,6a,7-tetrahydro-1,9-dihydroxy-2,10-dimethoxy-6-(3-methylbut-2-enyl)-4H-dibenzo(de,g)quinoline is prepared in the following manner:

1.38 g. (4.37 mmol) (—)-7-Hydroxy-1-(3-hydroxy-4-methoxybenzyl)-6-methoxy-1,2,3,4-tetrahydroisoquinoline in 25 ml. anhydrous ethanol is mixed with 0.9 g. (10.7 mmol) sodium bicarbonate, 0.44 g. (4.2 mmol) 1-chloro-3-methylbut-2-ene and 100 mg. potassium iodide. The reaction mixture is allowed to react for 1 hour at ambient temperature and for 4 hours at 80° C. The usual working up and chromatographic purification on silica gel with chloroform as elution agent gives (3-hydroxy-4-methoxybenzyl)-6-methoxy-2-(3-methylbut-2-enyl)-1,2,3,4-tetrahydroisoquinoline in the form of a yellowish foam.

MS: m/e 383 (M+), base peak m/e 246.

6.49 g. (16.9 mmol) (—)-7-Hydroxy-1-(3-hydroxy-4-methoxybenzyl)-6-methoxy-2-(3-methylbut-2-enyl)-1,2,3,4-tetrahydroisoquinoline are then reacted in 55 ml. trifluoroacetic acid and 55 ml. anhydrous methylene chloride with 2.3 ml. (4.23 g., 24.4 mmol) vanadium oxytrichloride at −10° C. in a manner analogous to that described in Example 1. The (+)-5,6,6a,7-tetrahydro-1,9-dihydroxy-2,10-dimethoxy-6-(2-methylbut-2-enyl)-4H-dibenzo(de,g)quinoline obtained upon working up can, without further purification, be used in the subsequent methylation.

EXAMPLE 4

(+)-5,6,6a,7-Tetrahydro-1,2,9,10-tetramethoxy-6-(2-methylprop-2-enyl)-4H-dibenzo(de,g)quinoline 5.7 g. (18.07 mmol) (—)-7-Hydroxy-1-(3-hydroxy-4-methoxybenzyl)-6-methoxy-1,2,3,4-tetrahydroisoquinoline and 3.7 g. (44 mmol) sodium bicarbonate in 120 ml. ethanol are mixed with 1.76 ml. (1.64 g., 18,07 mmol) 3-chloro-2-methylprop-1-ene. The mixture is allowed to react for 30 minutes at ambient temperature and thereafter for 3 hours at 80° C., while stirring. The usual working up and chromatographic purification on silica gel with chloroform as elution agent gives (+)-7-hydroxy-1-(3-hydroxy-4-methoxybenzyl)-6-methoxy-2-(2-methylprop-2-enyl)-1,2,3,4-tetrahydroisoquinoline in the form of a TLC-uniform yellowish foam.

3.0 g. (8.12 mmol) of the material obtained above are dissolved in a mixture of 25 ml. trifluoroacetic acid and 25 ml. anhydrous methylene chloride and reacted at −10° C., at intervals of 10 minutes, with 2×0.41 ml. (1.5 g., 8.80 mmol) vanadium oxytrichloride analogously to the method described in Example 1. Appropriate working up gives (+)-5,6,6a,7-tetrahydro-1,9-dihydroxy-2,10-dimethoxy-6-(2-methylprop-2-enyl)-4H-dibenzo(de,g)quinoline in practically quantitative yield in the form of a TLC uniform yellowish foam which is O-methylated in toluene/dimethylformamide with phenyltrimethylammonium hydroxide analogously to the method described in Example 1. Appropriate working up and chromatography of the crude product on silica gel with chloroform as elution agent gives (+)-5,6,6a,7-tetrahydro-1,2,9,10-tetramethoxy-6-(2-methylprop-2-enyl)-4H-dibenzo(de,g)quinoline in the form of a yellowish foam. Treatment with an ethanolic hydrochloric acid solution gives the crystalline hydrochloride; m.p. 195°–208° C.

MS: m/e 395 (M+) NMR: δ(DMSO-d₆) 2.0 (s, CH₃), 3.66 (1−OCH₃), 3.80–3.88 (3×OCH₃), 5.37 (m, 2H), 6.93 (s, 1H), 7.05 (s, 1H), 7.96 (11−H).

$[\alpha]_D = +90.2°$ (c=0.5, chloroform)

L-(+)-tartrate: m.p. 103°–118° C. (crystallised from methanol-isopropanol-acetone). $C_{24}H_{29}NO_4 \cdot C_4H_6O_6 \cdot 1\frac{1}{4}H_2O$ calc: C 59.19%; H 6.65%; N 2.46% found: 59.03%; 6.49%; 2.46%

EXAMPLE 5

(+)-6-Cyclopropylmethyl-5,6,6a,7-tetrahydro-1,2,9,10-tetramethoxy-4H-dibenzo(de,g)quinoline 16.2 g. (48.9 mmol) (−)-7-Hydroxy-1-(3-hydroxy-4-methoxybenzyl)-6-methoxy-1,2,3,4-tetrahydroisoquinoline, 8.2 g. (100 mmol) sodium bicarbonate and 500 mg. potassium iodide are dissolved in 200 ml. anhydrous ethanol and mixed with 4.5 ml. (4.44 g., 49 mmol) chloromethylcyclopropane. The reaction mixture is boiled under reflux for 40 hours in an inert gas atmosphere. The usual working up and chromatographic separation of unreacted starting material on silica gel with chloroform as elution agent gives (+)-2-cyclopropylmethyl-7-hydroxy-1-(3-hydroxy-4-methoxybenzyl)-6-methoxy-1,2,3,4-tetrahydroisoquinoline; m.p. 70°–81° C. (recrystallised from methanol/diethyl ether/hexane).

MS: molecular weight 383; m/e EI 232; m/e CI 384 $[\alpha]_D = +70.0°$ (c=0.5, chloroform).

4.5 g. (11.7 mmol) of the above-obtained material are reacted in a manner analogous to that described in Example 1 in a mixture of 40 ml. trifluoroacetic acid and 40 ml. anhydrous methylene chloride at −10° C. with 1.2 ml. (12.7 mmol) vanadium oxytrichloride. Appropriate working up of the reaction mixture gives (+)-6-cyclopropylmethyl-5,6,6a,7-tetrahydro-1,9-dihydroxy-2,10-dimethoxy-4H-dibenzo(de,g)quinoline; m.p. 80°–84° C. (recrystallised from ethanol/diethyl ether). MS: m/e 381 (M+).

Methylation of the above-obtained material with phenyltrimethylammonium hydroxide and working up in a manner analogous to that described in Example 1 gives (+)-6-cyclopropylmethyl-5,6,6a,7-tetrahydro-1,2,9,10-tetramethoxy-4H-dibenzo(de,g)quinoline in the form of the hydrochloride; m.p. 222°–235° C.

MS: m/e 395 (M+) $C_{24}H_{29}NO_4 \cdot HCl \cdot \frac{1}{4}H_2O$ calc.: C 66.05%; H 7.04%; Cl 8.12%; N 3.20% found: 65.81%; 6.89%; 7.62%; 3.00% $[\alpha]_D^{22} = +45°$ (c=0.5, chloroform) NMR: (CDCl₃) 0.5–1.5 (m, 5H, cyclopropyl-H), 3.70 (1−OCH₃), 3.96 (3×OCH₃), 6.67 (s, 8−H), 6.80 (s, 3−H), 8.07 (s, 11−H).

EXAMPLE 6

(±)-6-(Prop-2-ynyl)-5,6,6a,7-tetrahydro-1,2,9,10-tetramethoxy-4H-dibenzo(de,g)quinoline 12.0 g. (2.7 mmol) (±)-5,6,6a,7-Tetrahydro-1-hydroxy-2,9,10-trimethoxy-4H-dibenzo(de,g)quinoline are dissolved in 25 ml. ethanol and mixed with 560 mg. sodium bicarbonate and 0.26 ml. (2.95 mmol) propargyl bromide. The reaction mixture is stirred for 1 hour at ambient temperature and then for 2 hours at 80° C. under reflux. The usual working up and crystallisation from ethanol gives (±)-6-propargyl-5,6,6a,7-tetrahydro-1-hydroxy-2,9,10-trimethoxy-4H-dibenzo(de,g)quinoline;

m.p. 135°–150° C. MS: m/e 365 (M+), 40 (base peak) Hydrochloride: m.p. 172°–180° C.

Methylation of the above-described product with phenyltrimethylammonium hydroxide and working up in a manner analogous to that described in Example 1 gives (±)-6-(prop-2-ynyl)-5,6,6a,7-tetrahydro-1,2,9,10-tetramethoxy-4H-dibenzo(de,g)quinoline in the form of the hydrochloride; m.p. 224°–232° C.

MS: m/e 379 (M+), 339 (base peak) $C_{23}H_{25}NO_4 \cdot HCl$ calc.: C 66.42%; H 6.30%; Cl 8.52%; N 3.37% found: 66.28%; 6.35%; 8.70%; 3.29%

Starting from optically-active 5,6,6a,7-tetrahydro-1-hydroxy-2,9,10-trimethoxy-4H-dibenzo(de,g)quinoline, there is obtained, with the same reaction sequence, the corresponding enantiomeric hydrochloride; m.p. 170°–182° C.

dextrorotary hydrochloride: $[\alpha]_D^{22} = +161°$ (c=0.5; chloroform)

laevorotary hydrochloride: $[\alpha]_D^{22} = -157°$ (c=0.5; chloroform).

We claim:

1. Dibenzo(de,g)quinoline derivatives of the general formula:

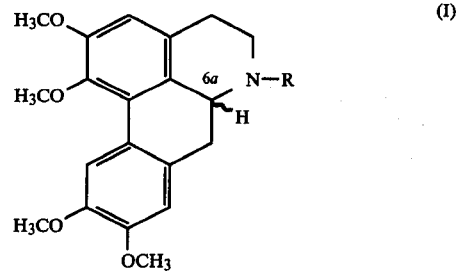

(I)

wherein R is an unsaturated aliphatic hydrocarbon radical containing up to 6 carbon atoms or a cycloalkylalkyl radical containing 4 to 6 carbon atoms; and the pharmacologically-acceptable salts thereof.

2. Dibenzo(de,g)quinoline derivatives according to claim 1, wherein R is an unsaturated aliphatic hydrocarbon radical containing 3 to 6 carbon atoms or a cycloalkylalkyl radical containing 4 to 6 carbon atoms.

3. Dibenzo(de,g)quinoline derivatives according to claim 1 or 2, wherein R is an allyl, methallyl, dimethylallyl, but-2-enyl, 3-methylbut-3-enyl, propargyl, cyclopropylmethyl, cyclobutylmethyl or cyclopentylmethyl radical.

* * * * *